(12) United States Patent
de Clerck

(10) Patent No.: US 9,999,510 B2
(45) Date of Patent: Jun. 19, 2018

(54) METHOD FOR MANUFACTURING A TEMPLATE TO ADAPT THE SHAPE OF A BONE DEFECT IN A JAW TO A BONE SUPERSTRUCTURE

(71) Applicant: DENTAL VISION B.V.B.A., Tervuren (BE)

(72) Inventor: René de Clerck, Tervuren (BE)

(73) Assignee: DENTAL VISION B.V.B.A., Tervuren (BE)

( * ) Notice: Subject to any disclaimer, the term of this patent is extended or adjusted under 35 U.S.C. 154(b) by 454 days.

(21) Appl. No.: 14/405,845

(22) PCT Filed: Jun. 5, 2013

(86) PCT No.: PCT/BE2013/000027
§ 371 (c)(1),
(2) Date: Dec. 5, 2014

(87) PCT Pub. No.: WO2013/181721
PCT Pub. Date: Dec. 12, 2013

(65) Prior Publication Data
US 2015/0150684 A1    Jun. 4, 2015

(30) Foreign Application Priority Data

Jun. 5, 2012   (BE) .................................. 2012/0378
Jul. 3, 2012    (BE) .................................. 2012/0453

(51) Int. Cl.
*A61F 2/30*   (2006.01)
*A61F 2/28*   (2006.01)
(Continued)

(52) U.S. Cl.
CPC ...... *A61F 2/30942* (2013.01); *A61B 17/1673* (2013.01); *A61B 17/176* (2013.01);
(Continued)

(58) Field of Classification Search
CPC ... A61F 2/30942; A61F 2/2803; B33Y 10/00; B33Y 80/00; A61B 34/10;
(Continued)

(56) References Cited

U.S. PATENT DOCUMENTS 4,917,604 A    4/1990 Small
5,306,149 A    4/1994 Schmid et al.
(Continued)

FOREIGN PATENT DOCUMENTS

DE          19907420 A1    9/2000
DE       102006047054 A1   4/2008
(Continued)

*Primary Examiner* — Nicholas Lucchesi
(74) *Attorney, Agent, or Firm* — Browdy and Neimark, PLLC

(57) ABSTRACT

A method is provided for manufacturing a template, whereby a digital or physical model of the shape of at least a part of the jaw is generated. A desired shape for the jaw bone for positioning a bone superstructure is compared to the model and a bone part of the jaw bone is identified, which bone part is to be removed in order to approach the desired shape. A guide surface is provided on the template to guide a milling element in order to remove the identified bone part. A bone superstructure is also described.

17 Claims, 4 Drawing Sheets

(51) Int. Cl.

| | | |
|---|---|---|
| *A61B 17/17* | (2006.01) | |
| *A61C 1/08* | (2006.01) | |
| *B33Y 10/00* | (2015.01) | |
| *B33Y 80/00* | (2015.01) | |
| *A61C 13/00* | (2006.01) | |
| *A61C 8/00* | (2006.01) | |
| *A61B 17/16* | (2006.01) | |
| *A61C 8/02* | (2006.01) | |
| *A61B 34/10* | (2016.01) | |

(52) U.S. Cl.
CPC .............. *A61B 34/10* (2016.02); *A61C 1/084* (2013.01); *A61C 8/0031* (2013.01); *A61C 13/00* (2013.01); *A61F 2/2803* (2013.01); *B33Y 10/00* (2014.12); *B33Y 80/00* (2014.12); A61B 17/1615 (2013.01); A61B 2017/1602 (2013.01); A61B 2034/102 (2016.02); A61B 2034/108 (2016.02); A61C 8/0006 (2013.01); A61F 2002/3097 (2013.01); A61F 2002/30957 (2013.01); A61F 2002/30968 (2013.01); A61F 2002/30985 (2013.01)

(58) Field of Classification Search
CPC ... A61B 17/1673; A61B 17/176; A61C 1/084; A61C 8/0031; A61C 13/00
See application file for complete search history.

(56) References Cited

U.S. PATENT DOCUMENTS

| | | | |
|---|---|---|---|
| 5,320,529 | A | 6/1994 | Pompa |
| 5,759,033 | A | 6/1998 | Elia |
| 5,839,899 | A | 11/1998 | Robinson |
| 6,244,868 | B1 | 6/2001 | Schappert |
| 6,319,006 | B1 | 11/2001 | Scherer et al. |
| 2005/0170311 | A1* | 8/2005 | Tardieu ................ A61C 8/0089 433/76 |
| 2008/0287953 | A1* | 11/2008 | Sers ........................ A61C 1/084 606/87 |
| 2011/0151399 | A1* | 6/2011 | De Clerck ............. A61C 1/084 433/75 |
| 2013/0023888 | A1* | 1/2013 | Choi ...................... A61C 1/084 606/96 |
| 2013/0071811 | A1* | 3/2013 | Groscurth ............. A61C 1/084 433/75 |
| 2013/0302752 | A1* | 11/2013 | Schneider ............. A61C 1/084 433/173 |
| 2014/0099599 | A1* | 4/2014 | Harrison ................ A61C 8/005 433/173 |
| 2015/0351866 | A1* | 12/2015 | Thompson, Jr. ........ A61C 1/084 433/173 |
| 2016/0106518 | A1* | 4/2016 | Choi ...................... A01N 59/04 433/75 |
| 2016/0184068 | A1* | 6/2016 | Chodorow ............. A61C 1/084 433/71 |
| 2016/0256236 | A1* | 9/2016 | Oppenheimer ........ A61C 1/084 433/75 |
| 2016/0374778 | A1* | 12/2016 | Grobbee ................ A61C 1/084 433/74 |

FOREIGN PATENT DOCUMENTS

| | | |
|---|---|---|
| EP | 1404244 B1 | 3/2009 |
| FR | 2753366 A1 | 3/1998 |
| GB | 2324470 A | 10/1998 |
| WO | 9114404 A1 | 10/1991 |
| WO | 9926540 A1 | 6/1999 |
| WO | 03003933 A1 | 1/2003 |
| WO | 2004112642 A2 | 12/2004 |
| WO | 2008043056 A2 | 4/2008 |
| WO | 2011075800 A1 | 6/2011 |
| WO | 2013040532 A1 | 3/2013 |

* cited by examiner

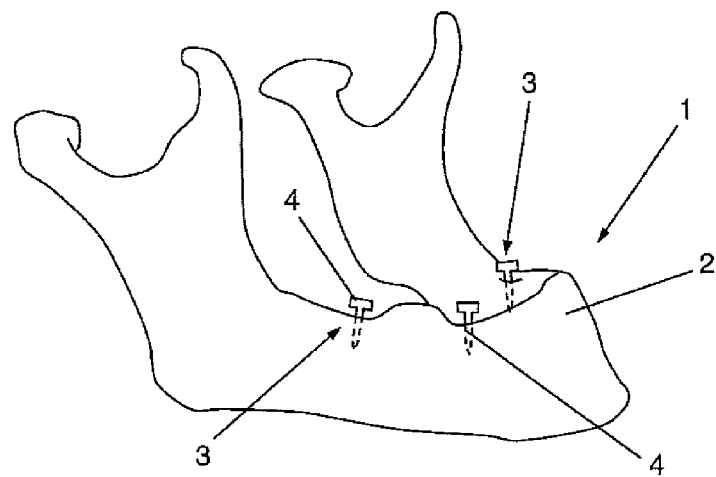
*Fig. 1*
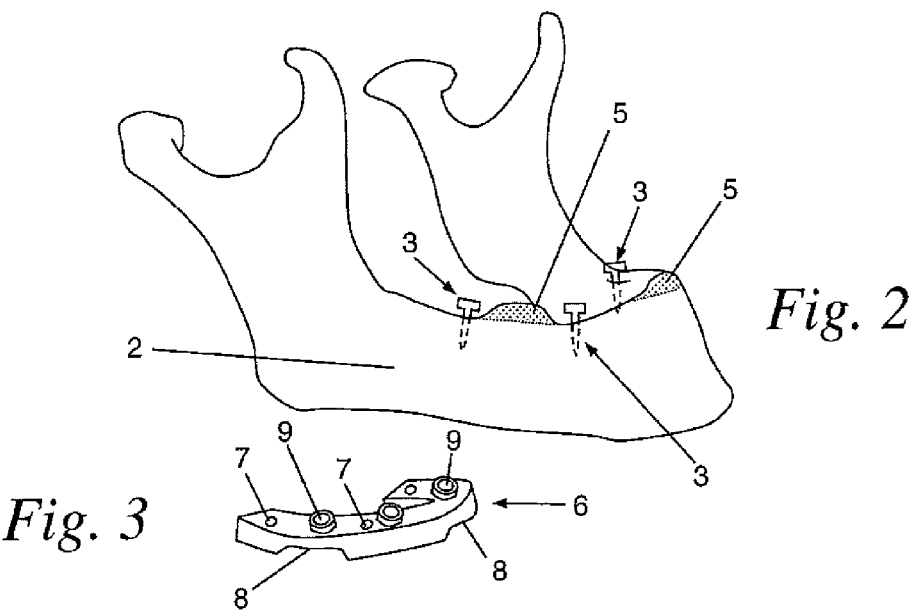
*Fig. 2*
*Fig. 3*
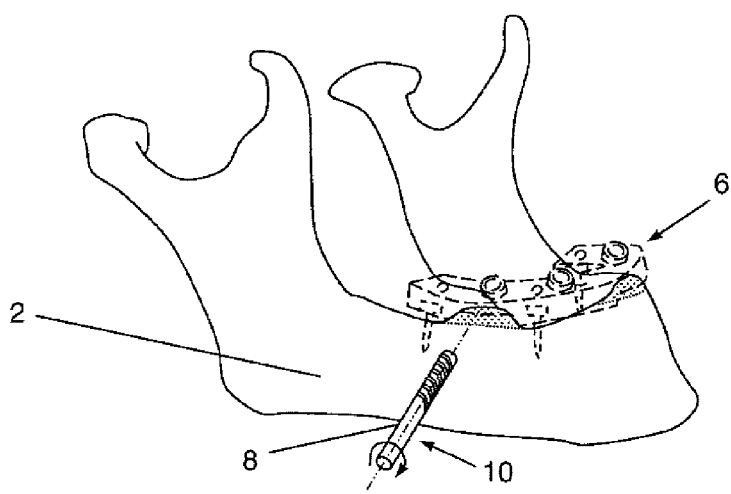
*Fig. 4*

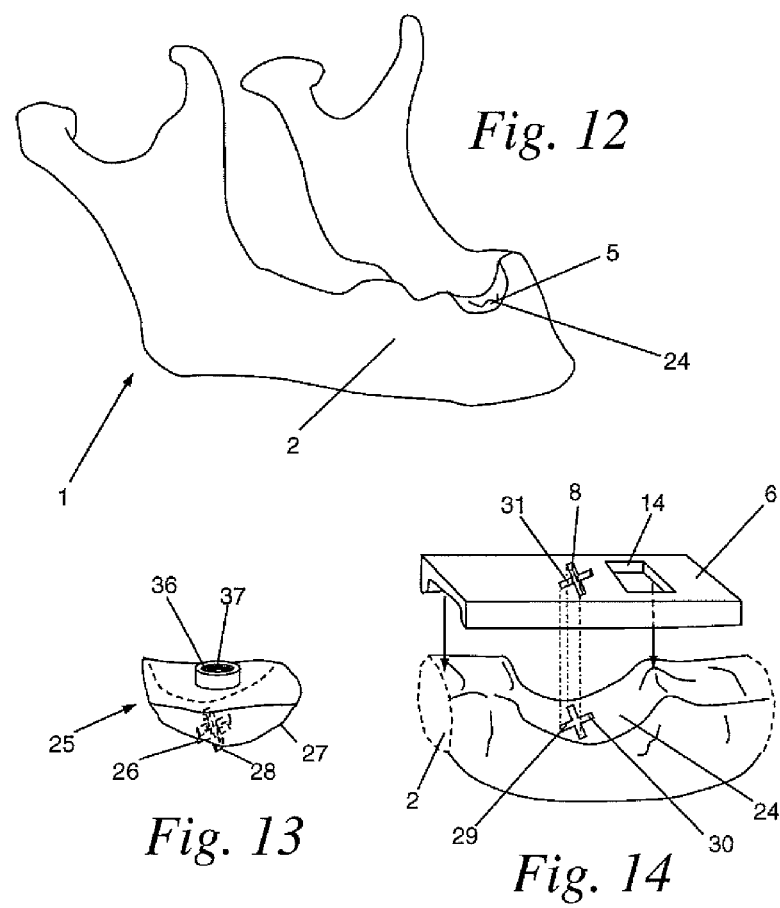
Fig. 12
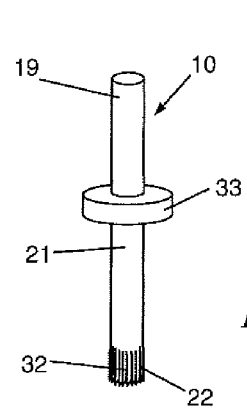
Fig. 13
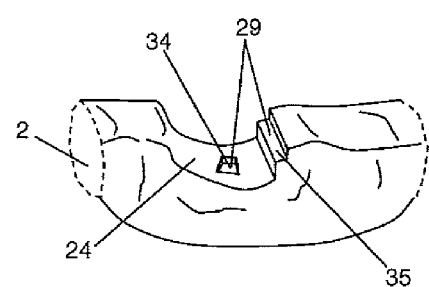
Fig. 14
Fig. 15
Fig. 16

METHOD FOR MANUFACTURING A TEMPLATE TO ADAPT THE SHAPE OF A BONE DEFECT IN A JAW TO A BONE SUPERSTRUCTURE

The invention concerns a method for manufacturing a template, whereby a digital or physical model of the shape of at least a part of the jaw bone of an upper or lower jaw in which a bone defect is present is generated and a geometry for a bone superstructure is determined in order to correct said bone defect. Taking into account the data of this model, the template is manufactured in such a way that it can be positioned in the jaw in a fixed position, whereby at least one guide surface is provided on the template for guiding a milling element.

When a dental prosthesis must be positioned in a jaw in a position where the jaw's bone has been resorbed, and a bone defect was thus formed, a bone graft is usually provided in order to fill the bone defect, or this bone defect is filled with artificial bone and covered with a membrane. After the bone defect is thus repaired, the dental prosthesis can be manufactured and possibly one or several dental implants can be placed in the jaw in which the dental prosthesis is to be mounted.

Such systems are described for example in documents DE 199 07 420, FR 2 753 366, U.S. Pat. Nos. 5,306,149, 5,759,033, 5,839,899, 6,244,868, WO 2004/112642 and WO 91/14404.

At present, the aim is to minimize the number of different steps for placing implants in a jaw and for mounting a dental prosthesis on these implants as much as possible. Thus, we wish to mount a preferably definitive dental prosthesis immediately after placing one or several implants in a jaw.

With the emergence of digital three-dimensional imaging techniques, CADCAM and rapid prototyping production methods, it is now possible to manufacture a bone superstructure for a bone defect on the basis of a three-dimensional image, obtained for example by performing a CT scan, whereby this bone superstructure can be placed in the bone defect in order to fill the latter.

When it is required, however, to provide an implant in the position of a bone defect in order to mount a dental prosthesis, means are provided on the bone superstructure for fixing the dental prosthesis, in particular a connection element.

Thus, in document WO 2011/075800, a conical recess is provided for example in the bone superstructure in which is placed a dental implant for carrying a dental prosthesis.

Since, at present, the planning for the placement of dental implants and the design of the dental prosthesis which is to be mounted on these implants take place before these implants are put in the jaw, it is of great importance that these implants are very accurately placed in the planned position. To this end, a template is manufactured which makes it possible to provide bore holes in the jaw in the planned position and to thus place implants in these bore holes in the jaw according to the planning.

Manufacturing a template by applying for example a rapid-prototyping technique on the basis of the data of a digital three-dimensional image of a jaw is already known as such. Such a template is used for drilling a bore hole in a specifically selected position and with a specific orientation in order to put an implant in this bore hole with a planned position and orientation. Said three-dimensional image is obtained for example by making a CT scan of the jaw. An appropriate method for this is described for example in U.S. Pat. No. 5,320,529 (Pompa), WO 99/26540 (Klein), U.S. Pat. No. 6,319,006 (Scherer et al.) and EP 1404244 (De Clerck).

If the dental prosthesis must be fixed in relation to the jaw in a position corresponding to a bone defect, it is thus required to place the corresponding bone superstructure, provided with a connection element for fixing the dental prosthesis, with great accuracy as well in a pre-planned position in the bone defect. However, according to the present state of the art, it is impossible to guarantee a sufficiently accurate placement of the bone superstructure, such that the connection element is situated precisely in a predetermined position in relation to the jaw.

The invention aims to remedy this by proposing a bone superstructure and a template with which this required accuracy can be achieved. Thus, the invention makes it possible to place a bone superstructure almost exactly in a pre-planned position in a bone defect. If the bone superstructure is also provided with means for fixing the dental prosthesis, these means are also positioned very accurately according to the pre-planned position in relation to the jaw and in relation to other dental implants which are possibly provided in the jaw as well.

To this aim, at least one positioning member is provided on the bone superstructure on a bone side thereof, whereby this bone side must connect to the bone of the jaw. Further, a desired shape is determined for the bone defect, whereby this shape exhibits a receiving element. This receiving element can be appropriately connected to said positioning member, such that said bone superstructure can be placed in a fitting and uniform manner in the bone defect with said desired shape. The desired shape for the bone defect is compared to said model of the part concerned of the jaw in order to identify at least a bone part of the jaw bone, which bone part must be removed in order to approach said desired shape. The above-mentioned guide surface is then provided on the template such that, after the template has been positioned on the jaw, this guide surface makes it possible to guide a milling element in order to remove the identified bone part.

Practically, said positioning member forms one or several protrusions on the bone side of said bone superstructure, whereby said receiving element comprises a recess in the bone of the jaw in which the positioning device can be placed in an almost fitting manner.

The bone superstructure for at least partly filling a bone defect in a jaw, according to a preferred embodiment of the invention, has a bone side which must extend opposite to the bone surrounding said bone defect in order to connect to it, whereby this bone superstructure comprises at least one positioning member provided on said bone side.

Advantageously, the bone superstructure has at least one connection element provided on a free side thereof, which free side is opposite to said bone side, whereby this connection element makes it possible to fix a dental prosthesis to a bone superstructure.

Further, it is found that in some cases, the shape or the contours of the jaw's bone, in particular of the alveolar ridge, are not ideal for placing a dental prosthesis in this jaw. In that case it is indicated to remove for example a part of the jaw's bone. According to the present state of the art, this can be done in a rather artisanal way, after opening up the gums, by removing a part of the jaw's bone, for example by milling away the excess bone by means of a drill and thus remove it.

Naturally, such a method may lead to an incorrect execution as too much or too little of the jaw's bone is removed or as bone is milled away in the wrong position. Moreover, it will be often required, after adapting the shape of the jaw bone, to generate a new three-dimensional image of the jaw, for example by making an additional CT scan.

The present invention also allows to remedy these disadvantages by proposing a template and a method for manufacturing this template, making it possible to remove a predetermined part of the jaw bone in a controlled manner. Moreover, the template according to the invention also allows to make bore holes in the jaw in predetermined positions with a preselected orientation for placing dental implants in the jaw. On these implants can subsequently be fixed a dental prosthesis or a superstructure of a dental prosthesis.

To this aim, a digital or physical model of the shape of at least a part of the jaw bone of an upper or lower jaw is generated, and a desired or optimal shape of the jaw bone for placing a prosthetic element is compared to this model. Next, at least one bone part of this jaw bone is identified, which bone part must be removed in order to approach said desired or optimal shape. The above-mentioned guide surface is hereby provided on the template such that, after the template has been positioned in the jaw, this guiding element makes it possible to guide said milling element so as to remove the identified bone part.

Practically, the position and orientation of at least one bore hole are selected in the jaw bone for placing an implant, whereby an opening is provided in said template for guiding a drill for boring said bore hole. The position and orientation for this opening in the template is selected such that, when the template is positioned in the jaw in said fixed position, said bore hole can be provided by guiding a drill through said opening.

According to a variant embodiment of the method according to the invention, a recess is provided in the template in a position corresponding to said identified bone part, such that this identified bone part extends opposite to this recess or through this recess when the template is positioned in the jaw, whereby said guide surface extends along this recess. The guide surface preferably connects to the recess.

Advantageously, when generating said digital or physical model, reference elements are determined which are fixed in relation to the jaw's bone, whereby fastening elements are provided on said template making it possible to fix the template in a detachable manner to said reference elements when the template is positioned in the jaw in said fixed position.

According to an interesting embodiment of the method according to the invention, the position of said identified bone part is determined in relation to said reference elements, whereby, taking into account this relative position, said guide surface is provided on the template in a corresponding relative position with respect to said fastening elements. Thus, this guiding element makes it possible, after the template has been positioned in the jaw, to guide said milling element in order to remove the identified bone part.

Said model is preferably generated by making a three-dimensional image of said jaw. Said template is hereby made on the basis of said three-dimensional image by applying a rapid-prototyping technique.

According to a preferred embodiment of the method according to the invention, said guide surface is formed by the surface of a recess in the template on the side directed towards said jaw bone when the template is positioned in said fixed position in the jaw.

According to a special embodiment of the method according to the invention, said guide surface is provided with a metal coating extending according to said guide surface.

The invention concerns a milling element for removing a bone part from an upper or lower jaw by guiding this milling element over the guide surface of a template, whereby this guide surface extends on either side of the bone part to be removed. This milling element consists of a drill with a first far end which must co-operate with a drive element so as to subject the bore around its axis to a rotary motion, whereby the opposite far end of the bore has a smooth surface and, connecting to this smooth surface, a cutting surface. On the side opposite to said far end and connecting to the cutting surface is hereby preferably also provided a smooth surface.

Other particularities and advantages of the invention will become clear from the following description of a few specific embodiments of the method, the template and the bone superstructure according to the invention. This description is given as an example only and does not limit the scope of the claimed protection in any way; the following reference numbers relate to the accompanying figures.

FIG. 1 is a schematic view in perspective of a lower jaw provided with reference elements.

FIG. 2 represents the lower jaw from FIG. 1 whereby bone parts are identified.

FIG. 3 is a schematic view in perspective of a template provided with guide surfaces.

FIG. 4 represents the lower jaw from FIGS. 1 and 2 on which the template from FIG. 3 has been mounted.

FIG. 12 is a schematic view in perspective of a lower jaw with a bone defect.

FIG. 13 is a schematic view in perspective of a bone superstructure according to an interesting embodiment according to the invention.

FIG. 14 is a schematic view in perspective of a part of the lower jaw with the bone defect from FIG. 12 with a portion of a template according to the invention.

FIG. 15 is a schematic view in perspective of a milling element according to an embodiment of the invention.

FIG. 16 is a schematic view in perspective of a part of the lower jaw with a bone defect with a desired shape according to another embodiment of the invention.

In the different figures, identical reference numbers refer to identical or analogous elements.

Figure 5:
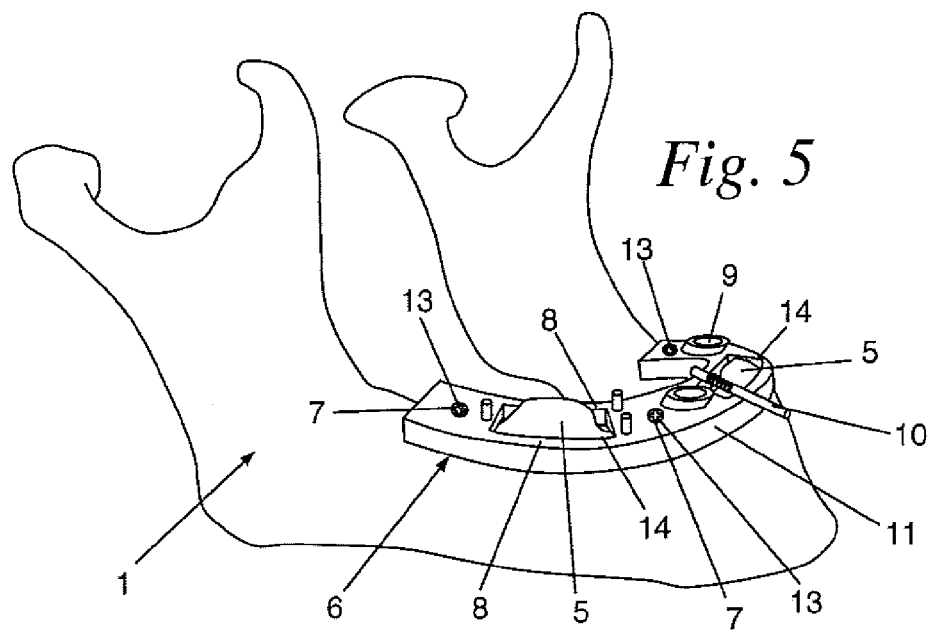
FIG. 5 is a schematic view in perspective of a lower jaw on which is positioned a basic piece of a template.

The invention generally concerns a template allowing to bore holes in the bone of a jaw for placing implants and/or to remove parts of the bone from this jaw.

For making bore holes, the template is provided with openings, in particular cylindrical openings, whose position and orientation have been defined beforehand. When the template is placed in the jaw, a bore can thus be guided through these openings so as to drill a hole in the jaw in which is subsequently placed an implant. Such a template is usually provided with several openings corresponding to different selected positions and orientations for implants which are to be fixed in the jaw. On the free far end of the implants protruding from the jaw, a prosthetic element is to be mounted such as for example a dental prosthesis.

In some cases, however, it is desirable to remove a portion of the jaw bone, for example so as to facilitate the insertion of implants or to adapt the jaw bone such that an optimal situation is obtained for placing a dental prosthesis. The part of the jaw bone to be removed is taken away by means of a milling element such as for example a drill or a saw. In order to remove this bone with the required accuracy and to thus remove bone from the desired position without milling away too much or too little bone, a guide surface is provided on said template which makes it possible to guide the milling element. Naturally, the jaw's bone is exposed by making an incision in the corresponding gum before said part of the bone is milled away.

The template according to the invention is preferably made by means of a so-called rapid prototyping or 3D printing technique such as, for example, selective laser sintering or melting, stereolithografy, fused deposition modelling, etc. A 3D-CAD model is hereby for example taken as a basis for the template which was designed on the basis of a digital three-dimensional image of the jaw, obtained by making a CT scan. Such methods for manufacturing a template are already sufficiently well known to those skilled in the art. Advantageously, such a template is made for example by milling it from a block of polyether ether ketone (PEEK) in a computer-controlled manner.

FIG. 1 represents a patient's lower jaw 1. In the bone 2 of this jaw 1 are fixed three reference elements 3. In the given embodiment, each of these reference elements 3 is formed of a little screw 4 having a length of for example some 5 mm. These screws 4 are simply screwed through the gum in the bone 2 of the jaw 1, such that the head of the screws 4 extends at least partly above the gum.

The reference elements, in particular the screws 4, are clearly visible when a three-dimensional image of the jaw is generated by making for example a CT scan. This three-dimensional image thus forms a digital model of the jaw.

According to a preferred embodiment of the method according to the invention, such a CT scan of the jaw 1 with the reference elements 3 is made in order to obtain a three-dimensional digital image of the jaw 1.

In this digital three-dimensional image, the bone 2 of the jaw 1 is clearly visible, together with the reference elements 3, in particular the screws 4, and critical anatomical structures such as for example nerves, blood vessels, bone structure or geometry of the bone.

Starting from the thus generated three-dimensional digital image, according to a preferred embodiment of the method, an optimal position and orientation are subsequently selected for the implants to be placed in the jaw 1, taking into account the position of said critical anatomical structures in order to achieve a sufficiently firm anchoring of the implants in the bone 2 without the latter extending for example through said nerves.

Further, when selecting the position of the implants, also the geometry of the dental prosthesis to be made is preferably taken into account, which is for example at least partly CAD-designed on the basis of said three-dimensional digital image.

Starting from the selected position and orientation of the implants, a position and orientation of a bore hole in the jaw bone 2 for placing each of the implants is thus selected. The position and orientation of these bore holes is determined in relation to the reference elements 3.

Further, the observed shape of the jaw bone 2 in the generated three-dimensional image of the jaw 1 of the corresponding digital model thereof is compared to a desired shape of the jaw bone 2. This desired shape is optimal for placing the implants and/or for placing a prosthetic element, such as a dental prosthesis, on the jaw 1. Bone parts 5 of the bone 2 of the jaw 1 are hereby identified, as is schematically represented in FIG. 2, which must be removed in order to approach the desired shape of the jaw bone 2 as much as possible. The position of these identified bone parts 5 is preferably also defined in relation to the reference elements 3. The identified bone parts 5 are usually situated in the alveolar bone and may for example consist of exostoses situated on or near the alveolar ridge. These bone parts to be removed extend for example on the buccal, lingual, palatal or occlusal side of the jaw bone.

When identifying the bone parts 5 to be removed, also a section is determined forming the separation between the bone part 5 to be removed and the bone 2 of the jaw 1 to be preserved.

Next, a template is made, preferably by means of a rapid prototyping technique, such that it can be placed in a fixed position in the jaw. An example of a template 6 according to the invention is schematically represented in FIG. 3. When use is made of reference elements 3, such as screws 4, according to an interesting embodiment of the method, fastening elements 7 are provided on the template 6 making it possible to fasten the latter in a detachable manner to these reference elements 3 in a fixed position in relation to the jaw 1. Such a template which is fixed to reference elements is already described for example in document WO 03/003933.

Further, a guide surface 8 for guiding a milling element is provided on the template. The location of this guide surface 8 on the template is determined on the basis of the relative position of a corresponding identified bone part 5 such that, after the template has been positioned in the jaw 1, this guiding element 8 extends opposite this identified bone part 5. Along this guide surface 8 is then guided a milling element, such as for example a drill, in order to remove the identified bone part 5.

The guide surface 8 is formed in particular of the surface of a recess in the template 6 on the side which is directed towards the bone 2 of the jaw 1 when the template 6 is positioned in the jaw 1. In this position, the guide surface 8 extends at least partly, preferably almost parallel to said section forming the separation between the bone part 5 to be removed and the bone 2 of the jaw 1 to be preserved.

Thus, for each identified bone part 5, a guide surface 8 is provided on the template 6 such that, after the template has been put in a fixed position in the jaw 1, each of the identified bone parts 5 can be removed.

Further, in this embodiment of the method according to the invention, one or several openings 9 are provided in the template 6 in order to guide a drill for drilling a bore hole in the jaw 1 for placing implants. A position and orientation for each of these openings 9 are hereby preferably selected such that, when the template 6 has been positioned in the jaw 1 in said fixed position, the bore holes can be provided by guiding a drill through each of the openings 9. When manufacturing the template 6, the position and orientation of the bore holes in relation to said fastening elements 7 are defined in accordance with the above-mentioned position and orientation of the bore holes in relation to the reference elements 3. The provision of such bore holes in a template which is fixed in a detachable manner on reference elements has already been described in WO 03/003933.

FIG. 4 represents the situation in which the template 6, illustrated by means of a broken line, has been placed in the jaw 1. Said fastening elements 7 are hereby formed of cylindrical openings extending through the template. Through these cylindrical openings, a screw is connected to the head of the screws 4, forming the reference elements 3, such that the template is mounted in a detachable manner on the reference elements 3 in a fixed position in relation to the jaw 1. To this end, the head of the screws 4, forming the reference elements 3, is provided for example with a cylindrical boring with internal screw thread.

After the template 6 has thus been fixed via the fastening elements 7 on the reference elements 3 of the jaw 1, the identified bone parts 5 can be removed. To this end, a milling element 10 is guided along each of the guide surfaces 8 while being subjected to a rotary motion around its axis. In the embodiment represented in FIG. 4, this milling element 10 consists for example of a drill 11 which is driven around its axis.

Naturally, when determining the position of the guide surface 8 on the template 6, the dimensions of the milling element 10 are taken into account. In the given example, the distance between the aforesaid section and the guide surface 8 is for example equal to the diameter of the drill 8.

Further, the bore holes for placing implants in a manner known as such are drilled by guiding a drill through said openings 9, and an implant is subsequently screwed in the jaw through each of these openings 9.

Further, it is also possible for example to provide a hard coating, in particular a metal coating on the guide surface 8 so as to avoid material being removed from the template 6 while performing the milling operation. This coating may assume all sorts of shapes and may consist for example of a metal foil which is attached to the guide surface by gluing or by a metal wire which is embedded in the guide surface. Of course, also non-metallic materials can be used therefore having sufficient resistance to the milling operation.

In the embodiment of the template 6 described above, the guide surface 8 is provided on a recess which opens freely into the bone 2 of the jaw 1. However, it is also possible for this guide surface 8 to be formed of a slot whose height corresponds for example to the diameter of the drill 11 which is used as a milling element 10. This slot hereby opens laterally in the bone 2 of the jaw 1 at the height of said section, such that the identified bone part 5 can be removed by guiding the drill through said slot.

Said guide surface 8 may also be provided in the template 6 in such a way that it allows for example to guide a guide pin fixed to a drill bit in which the milling element 10 has been mounted, whereby this drill head drives the milling element 10.

A milling element 10 must not necessarily consist of a drill 11, but it may of course assume any conventional form of a milling tool and may for example consist of a saw mill.

Further, the template may possibly consist of two parts. A first part of this template will then exhibit for example said fastening elements and said openings for making the bore holes for placing the implants. A second part of this template is then preferably fixed against the first part in a detachable manner and exhibits said guide surfaces for guiding a milling element so as to remove identified bone parts.

Neither is it necessary for the template 6 to have openings for making bore holes for placing implants, and it may for example have merely one or several guide surfaces for the removal of excess bone parts that have been identified.

A particularly interesting embodiment of the invention is represented in FIGS. 5 to 8. Hereby, after the identification of the bone parts 5 to be removed as described above, a template 6 is designed and manufactured consisting of two parts. A first part forms a basic piece 11 of the template 6, whereas a second part consists of a top piece 12.

FIG. 5 represents a basic piece 11 when it has been placed in a fixed position in a lower jaw 1 and attached to available reference elements in a detachable manner via fastening elements 7 by means of screws 13. This basic piece 11 is made, as in the above-described embodiment, on the basis of a three-dimensional model of the jaw, for example on the basis of a CT scan of the jaw. In the given example, two openings 9 are provided in the basic piece 11 for drilling bore holes for placing implants. Further, recesses 14 are provided whose position and dimensions are selected such that the identified bone parts 5 to be removed extend through these recesses 14 when the basic piece 11 has been positioned in the jaw 1.

As described in the preceding embodiment, when identifying the bone parts 5 to be removed, also a section is determined in relation to the reference elements 3 forming the separation between the bone part 5 to be removed and the bone 2 of the jaw 1 to be preserved.

In the embodiment of the invention represented in FIGS. 5 to 8, the basic piece 11 of the template 6 is made such that a guide surface 8 for a milling element 10 extends adjacent to said recesses 14. This guide surface 8 is defined in relation to the fastening elements 7 of the template 6 and extends, in the given example, on either side of the recesses 14 on the lingual and vestibular side thereof. This guide surface 8 hereby extends in the plane of said section when the basic piece 11 of the template 6 has been positioned in the jaw.

When a template 6 is made for an upper jaw, said guide surface 8 preferably extends along the palatinal and vestibular side of the recess 14 concerned.

Thus, after positioning the basic piece 11 of the template 6, a milling element 10 will be guided over the guide surface 8 so as to remove the identified bone parts 5 along the determined section.

Figure 7:
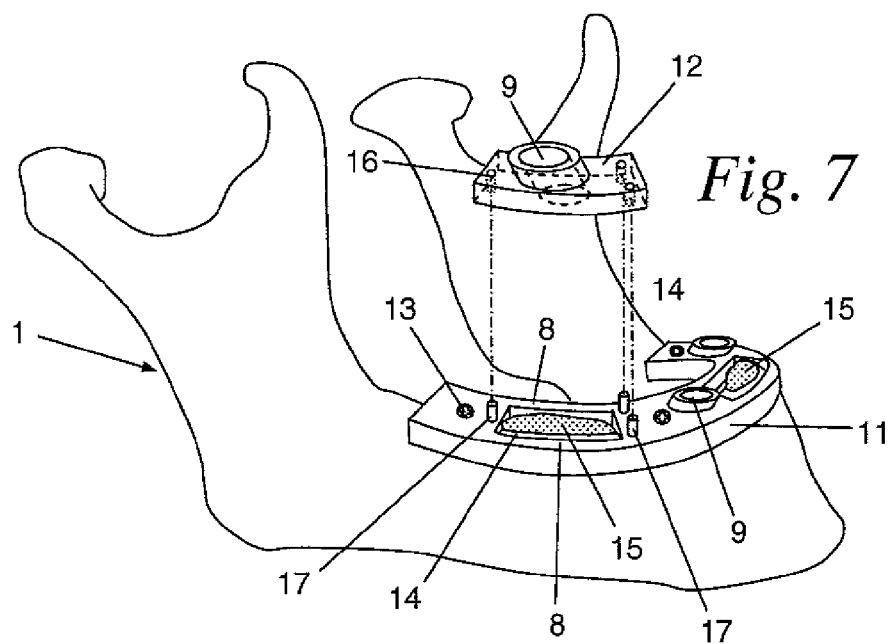
FIG. 7 is a schematic view in perspective of the lower jaw with the basic piece from FIG. 5 after identified bone parts have been removed.

FIG. 7 represents the situation after the bone parts 5 have thus been removed, whereby said sections 15 are consequently situated in the plane of the guiding surface 8.

When, during the design of the template 6 on the basis of among others the model, for example a three-dimensional digital image of the jaw, the position of the critical anatomical structures and possibly the geometry of the dental prosthesis to be made, it appears that an implant will have to be placed on or in the vicinity of a bone part 5 to be removed, a top piece 12 will also be made in addition to said basic piece 11.

Figure 6:
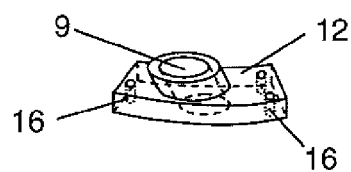
FIG. 6 is a schematic view in perspective of a top piece of the template from FIG. 5.

Such a top piece is schematically represented in FIG. 6. This top piece can be mounted on the basic piece 11 by means of mounting means provided to this end. These mounting means in particular allow to fasten the top piece 12 with high accuracy in a pre-determined position on the basic piece 11.

Further, this top piece has an opening 9 whose position and orientation correspond exactly to the selected position and orientation of the implant to be put in place when the top piece 12 is attached to the basic piece 11 and the latter has been positioned in the jaw.

In the given example of FIGS. 5 to 8, said mounting means are formed of parallel cylindrical bores 16 provided in the top piece 12 on the one hand, and of corresponding parallel cylindrical rods 17 extending on the top side of the basic piece 11 on the other hand.

Figure 8:
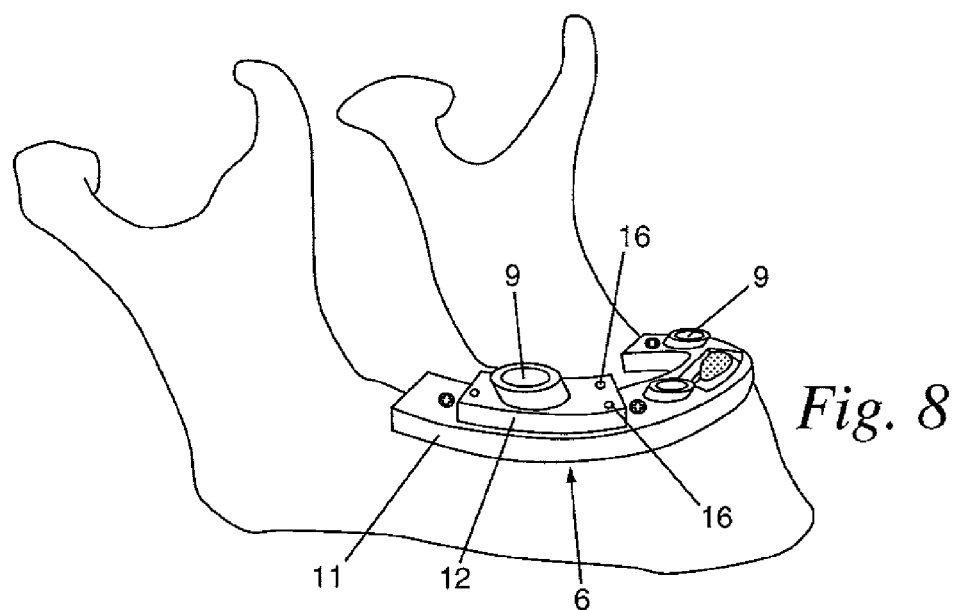
FIG. 8 is a schematic view in perspective of the lower jaw with the basic piece from FIG. 5, whereby the top piece is mounted on the base portion.

As is represented in FIGS. 7 and 8, after the removal of said bone parts 5, the top piece 12 is mounted on the basic piece 11 by fitting said rods 17 of the latter in the corresponding bore holes 16 of the top piece 12, such that said pre-determined position is reached.

Next, a bore hole is drilled for providing an implant with the required position and orientation through the opening 9 of the top piece 12.

Figure 9:
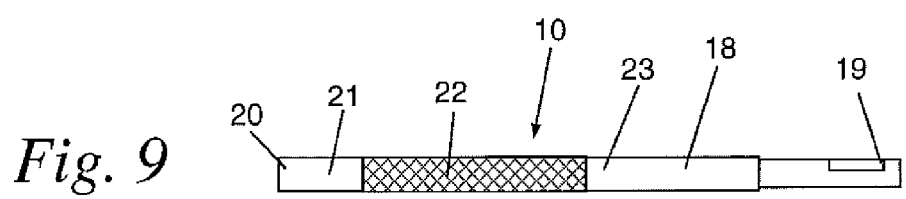
FIG. 9 is a schematic side view of a first embodiment of a milling element according to the invention.

The milling element 10 which is used in this embodiment of the invention preferably consists of a cylindrical drill 18 as represented in FIG. 9. This drill 18 has a first far end 19 which must co-operate with a drive element and is thus fit to be mounted in a drill head so as to subject the drill to a rotary motion around its axis. The opposite far end 20 of the drill 18 has a smooth cylindrical surface 21. Adjacent to this smooth surface 21, the drill has a cylindrical cutting surface 22 for milling bone. On the side opposite to said far end 20, adjacent to the cutting surface 22, is also provided a cylindrical smooth surface 23.

Thus, said bone parts 5 are removed by the cutting surface 22 when the drill 18 with said smooth surfaces 21 and 23 is guided over the guide surface 8 on either side of said recess 14.

While removing said bone parts 5, the cutting surface 22 of the drill 18 thus moves over the recess 14 of the basic piece 11, whereas said smooth surfaces 21 and 23, extending on either side of the cutting surface 22, are guided by the guide surface 8 on either side of the recess 14 concerned.

Figure 10:
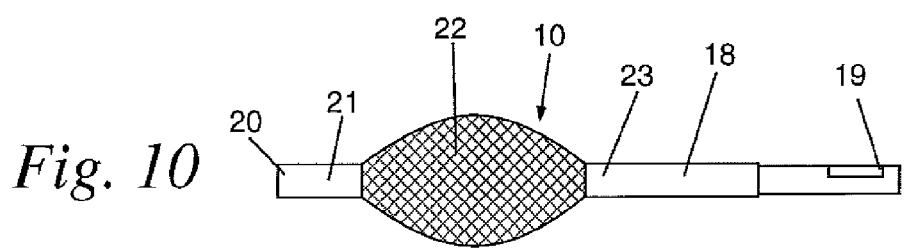
FIG. 10 is a schematic side view of a second embodiment of a milling element according to the invention.

FIG. 10 shows another embodiment of a milling element 10 according to the invention. This milling element 10 is different from the above-described milling element 10 in that the cutting surface 22 has the shape of a spheroid. Such a milling element 10 allows to obtain, during the removal of a bone part, a section which is bowl-shaped and thus approximates the shape of a tooth socket. By use of such a milling element can thus be ensured that bone is preserved in support of interdental papillae.

Figure 11:
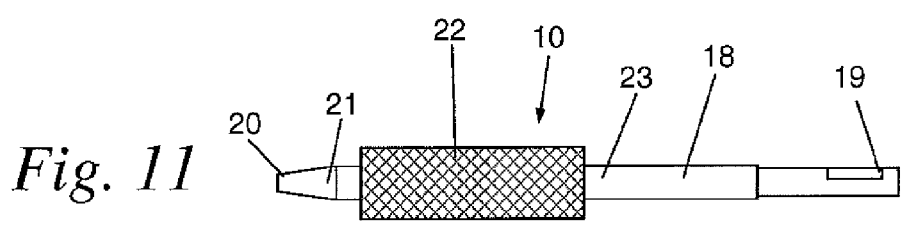
FIG. 11 is a schematic side view of yet another embodiment of a milling element according to the invention.

In yet another embodiment of this milling element 10, the cutting surface 22 is made cylindrical, but the diameter of this cutting surface 22 is larger than that of the drill 18 at the height of said smooth surfaces 21 and 22, as is represented in FIG. 11.

It should also be mentioned that the far end 20 of the drill 18 must not necessarily be made cylindrical, but that its diameter may for example decrease or that this far end may result in a point. Thus, said far end 20 of the drill 18 may have a conical shape.

Each of said smooth surfaces 21 and 23 of the milling element 10 may also be formed of an annular indentation which extends according to the circumference of the drill 18. In that case, the guide surface 8 of the template 6, with which this milling element 10 is to co-operate, is formed for example of a corresponding standing rib which fits in said indentation and over which this indentation is guided when performing the milling operation for the removal of the corresponding bone part 5.

Thus, the milling element 10 in general preferably consists of an axial symmetrical drill 18 having a cutting surface 22 connecting on either side to smooth surfaces 21 and 23.

If the template 6 is provided with a recess 14 for removing an identified bone part 5, the length of the cutting surface 22 according to the axial direction of the milling element 10 will preferably be smaller than the corresponding width of the recess 14 between the guide surfaces 8 extending on either side of this recess 14.

In the embodiments of the invention, the guide surface 8 which is provided on the template 6 extends according to a straight plane. However, it is also possible for this guide surface 8 to form a concave or convex curved surface. Neither does the section 15 necessarily extend in the plane of the correspondingly selected guide surface 8. In particular, this section 15 may have another shape and/or course than the guide surface 8, for example as a function of the type of milling element 10 which is used. Further, the section 15 may be parallel to the guide surface 8 when the template 6 has been positioned in the jaw, but this section may just as well be not parallel to the guide surface 8.

Although in the preceding embodiment of the invention, a template 6 is described having a basic piece 11 with merely one top piece 12, it is of course also possible for the template 6 to have two or more top pieces which can be mounted on a basic piece 11.

Moreover, in certain cases, the template 6 may have no top piece whatsoever and thus consist of the above-described basic piece 11 in which are provided recesses 14 for the removal of identified bone parts 5.

Neither are the mounting means restricted to the above-described mortise and tenon joint, but any connection system may be used which makes it possible to mount a top piece in a pre-determined position on a basic piece. Thus, the top piece may for example be fixed in bore holes by means of screws, provided in the basic piece. It is also possible for the top piece to have the negative form of a part of the basic piece so as to mount it on the latter in a fitting manner. The top piece may thus for example be glued on the basic piece in a pre-determined position.

In a variant of the preceding embodiments, which is not represented in the figures, an upstand is provided on the lingual or palatinal side of the template adjacent to the guide surface 8, forming a stop for the milling element 10. Thus is ensured, while milling, that the free far end 20 of the milling element 10, when it is guided over the guide surface, makes contact with said upstand. Thus, the position of the milling element according to its axial direction is controlled by the template as well.

This upstand or stop may possibly assume the shape of a slot in which the far end 20 of the milling element 10 is guided.

In the embodiments of the template as shown in the figures, it is fastened in a detachable manner to reference elements, such as screws, which are fixed in the jaw. However, these reference elements must not necessarily consist of screws; they may also be formed of teeth which are possibly still present in the jaw. In that case, the template may for example be temporarily glued onto these teeth during the milling operation, or said fastening elements may consist for example of the negative form of the occlusal plane of these teeth, such that the template can be placed in a fitting and relatively stable manner on these teeth.

According to an alternative method, reference elements are temporarily secured to teeth which are possibly present in the jaw.

In some situations, for example when it is necessary to temporarily remove the gum over a major part of the alveolar ridge, said reference elements may be formed of certain geometrical shapes of the jaw's bone at this alveolar ridge, whereby it is ensured that the shape of the template is suitable to be placed in a fitting manner on certain parts of this alveolar ridge, in a fixed position.

When the jaw 1 exhibits one or several bone defects, it is normally not possible to fix an implant in the jaw in a responsible manner at the level of these bone defects. Such bone defects are situated on the parts of a jaw where the jaw's bone has an insufficient height or too low a thickness to anchor an implant. In general, a bone defect indicates that this part of the jaw is too weak for fixing an implant in the bone thereof.

FIG. 12 represents a jaw 1 with a bone defect 24. At the height of this bone defect 24, the bone 2 of the jaw 1 has disappeared, for example due to bone resorption. If one wishes to place a dental prosthesis on one or several implants at the height of this bone defect 24, possibly between teeth which may still be present in the jaw 1, it is consequently required to fill this bone defect 24 and thus repair it so as to provide for a sufficient basis for the attachment of a dental prosthesis.

There are different techniques, known as such to someone skilled in the art, for filling a bone defect 24 so as to repair it before placing implants in the position of this bone defect 24. These techniques require a lot of time to make bone grow in this bone defect, however, during which period it is not possible yet to place implants.

According to the invention, in order to fill the bone defect 24, a bone superstructure 25 is designed and manufactured on the basis of for example a digital three-dimensional image generated from the jaw 1 with the bone defect 24. This three-dimensional image then makes it possible to generate a model of the jaw bone in which the bone defect 24 is present.

FIG. 13 represents such a bone superstructure 25, whereas FIG. 14 represents the corresponding bone defect 24 in which this bone superstructure 25 fits.

Starting from said model, the shape of the bone defect 24 is derived and a geometry is determined for the bone superstructure 25 in order to repair this bone defect 24. Further, at least one positioning member 26 is provided on the bone side 27 of the bone superstructure 25. This bone side 27 is formed of the part of the surface of the bone superstructure 25 which must connect to the bone 2 of the jaw 1 surrounding the bone defect 24.

The bone superstructure is then manufactured for example by applying a rapid prototyping technique such as for example selective laser sintering of titanium.

In the embodiment of the bone superstructure 25 represented in FIG. 13, said positioning member 26 is formed of a cross 28 consisting of two beam-shaped crossing ribs protruding in relation to the surface of the bone side of the bone superstructure 25.

The geometry of the bone side 27 of the bone superstructure 25 with the positioning member 26 defines a desired shape for the bone defect 24 so as to make it possible to place the bone superstructure 25 in a univocal and accurate pre-determined position in the bone defect 24 in order to repair it.

This desired shape for the bone defect 24 has a receiving element 29 which is to connect in a fitting manner to said positioning member 26 when the bone superstructure 25 has been placed in the bone defect 24. According to the embodiment of the invention as represented in FIGS. 13 and 14, this receiving element 29 is consequently formed of a cruciform recess 30 in which the cross 28 consisting of two beam-shaped crossing ribs can be placed in an accurately fitting manner.

In order to adapt the shape of the bone defect 24 in the jaw, a template 6 is manufactured which, as already mentioned above, can be placed in a fixed position in the jaw 1. By means of a milling element 10 which is guided through a guide surface 8 provided on the template 6, identified bone parts 5 are then removed in order to achieve the desired shape for the bone defect 24 in the jaw.

In order to design the template 6 with the guide surface, said desired shape for the bone defect is compared to the bone defect in said model of the jaw 1. At least one bone part of the jaw bone 2 is thereby identified which is to be removed in order to approach the desired shape for the bone defect 24. On the template, the guide surface 8 is then provided in such a position that, after the template 6 has been positioned in the jaw 1, this guide surface 8 makes it possible to guide the milling element 10 in order to remove the identified bone part.

In the given example in FIGS. 13 and 14, the guide surface 8 is consequently formed of the walls of a cruciform recess 31 in the template 6 whose dimensions match the corresponding positioning device 26 of the bone superstructure 25.

A milling element 10 which is fit for use to mill away identified bone part in order to create said receiving element 29 is represented in FIG. 15. Milling element 10 has a predominantly cylindrical shape and has a first far end 19 which should be mounted in the drill head of a drive element. The opposite far end 32 has a cutting surface 22 which allows to mill bone. Adjacent to the cutting surface 22, this milling element 10 has a smooth surface 21. Between both far ends there is a circular disc 33 whose central axis coincides with the axis of the milling element. In order to mill away thus identified bone parts, the milling element 10 is provided with the cutting surface 22 through said cruciform recess 31, such that the side of this disc 33 which is directed to said cutting surface 22 rests on the template 6 and said smooth surface 21 is guided through the guide surface 8, formed by the walls of the cruciform recess 31.

Further, the template 6 from FIG. 14 also has a recess 14 which makes it possible to remove a part of the bone from the bone ridge. Such a recess 14 with a guide surface extending on either side of this recess 14 has already been described above with reference to FIGS. 5 to 8.

FIG. 16 represents, by way of example, an alternative desired shape for a bone defect 24 in a jaw 1. In this example, the receiving element 29 consists of a prismatic recess 34 on the one hand and of a multi-stage relief 35 on the other hand. The corresponding bone superstructure, which is not represented, then has a corresponding positioning device with a prismatic protrusion and a negative shape of the relief 35.

In general, the bone superstructure 25 may be provided with a positioning member 26 having a geometric surface, such as a cylinder, a beam, a pyramid, a cone, a cube, a ring, a rib or a combination of one or several of these surfaces.

The size of successive cross sections of the positioning member 26 preferably decreases or remains constant as of said bone side 27 of the bone superstructure 25 up to the free far end of this positioning member 26. Thus, the positioning device is made for example at least partly conical.

The positioning device may also be formed of a for example cylindrical dowel made of a biocompatible or inert material. In that case is provided a corresponding, for example cylindrical recess on the bone side of the bone superstructure, whereas said receiving element is then formed for example of a corresponding cylindrical recess in the jaw's bone.

When designing the bone superstructure 25, possibly at least one connection element 36 may also be provided for mounting a dental prosthesis. In the embodiment of the bone superstructure 25 represented in FIG. 13, its side opposite to said bone side 27 exhibits a connection element 36. In the given example, this is formed by a cylindrical sleeve provided with internal screw thread 37. Naturally, also alternative embodiments of such a connection element 36, known as such, can be used without any problem.

The bone superstructure 25 may for example be made of titanium which preferably has an open structure and is possibly separated from the gum by a membrane which may be absorbable and which forms a barrier for the migration of epithelial cells. The bone superstructure 25 in general consists of a biocompatible material and is coated for example on the bone side thereof with a bone growth stimulating coating.

Further, means are preferably provided on the bone superstructure 25 making it possible to attach the latter to the bone 2 of the jaw 1. Thus, it may be provided for example with cylindrical bore holes through which the bone superstructure can be fixed to the jaw's bone in the bone defect by means of screws.

For clarity's sake is also mentioned that the principle of the manufacture, the composition and the operation of a template as described with reference to FIGS. 1 to 8 can also be applied to the template regarding the adjustment of a bone defect for placing a bone superstructure as described with reference to FIGS. 12 to 16 and vice versa.

Also, according to the invention, it is possible to manufacture a template which is provided with one or several openings 9 for providing bore holes for the placement of dental implants as well as with one or several guide surfaces in order to achieve a desired shape for a bone defect.

The invention claimed is:

1. A method for manufacturing a template, comprising:
generating a digital or physical model of a shape of at least a part of the jaw bone of an upper or lower jaw in which a bone defect is present,
determining a geometry for a bone superstructure to correct the bone defect,
using data of the model, making the template such that the template can be placed in a fixed position in the upper or lower jaw,
providing at least one guide surface on the template for guiding a milling element,
providing at least one positioning member on the bone superstructure on a bone side thereof to connect to the bone of the upper or lower jaw,
identifying a desired shape for the bone defect, the bone defect having a receiving element which is configured to connect in a fitting manner to said at least one positioning member, wherein the desired shape is identified such that said bone superstructure fits in said bone defect with said desired shape,
comparing said identified desired shape for the bone defect to said model,
identifying, as a result of the comparison, at least one bone part of the jaw bone to be removed to approach said desired shape,
providing said at least one guide surface on the template such that, after the template has been positioned in the upper or lower jaw, said at least one guide surface permits guiding of said milling element to remove the identified bone part.

2. The method according to claim 1, wherein the step of providing said at least one positioning member comprises forming a protrusion on said bone superstructure, and further comprising defining a recess in the bone of the upper or lower jaw to form said receiving element adapted to receive the at least one positioning member in a fitting manner.

3. The method according to claim 1, further comprises:
selecting a position and orientation for a bore hole in the jaw bone for placing at least one implant, and
defining an opening in said template to guide a drill for boring said bore hole,
wherein the step of selecting a position and orientation for this opening comprising, when the template has been positioned in the upper or lower jaw in said fixed position, cutting said bore hole by guiding a drill through said opening.

4. The method according to claim 3, wherein said template is manufactured from at least two parts, wherein a first part forms a basic piece configured to be positioned in said fixed position in the upper or lower jaw when in use and exhibits said at least one guide surface, whereas a second part forms a top piece in which said opening is defined, wherein the method further comprises providing a mounting means configured to mount the top piece in a predetermined position on the basic piece when in use.

5. The method according to claim 1, wherein, the step of generating said digital or physical model comprises fixing reference elements in relation to the bone of the upper or lower jaw, and providing fastening elements on said template configured to detachably attach the template to said reference elements when the template has been positioned in said fixed position in the upper or lower jaw.

6. The method according to claim 5, further comprising determining the position of said identified at least one bone part in relation to said reference elements, wherein the step of providing said at least one guide surface comprises, taking into account said relative position, providing said at least one guide surface on the template in a corresponding relative position in relation to said fastening elements, such that, after the template has been positioned in the upper or lower jaw, said at least one guide surface is in a position to guide said milling element to remove the identified at least one bone part.

7. The method according to claim 1, wherein the step of generating said digital or physical model comprises making a three-dimensional image of said upper or lower jaw, and making said template starting from said three-dimensional image by applying a rapid-prototyping technique.

8. The method according to claim 1, wherein said at least one guide surface is provided on a surface of a recess on a side of the template which is directed towards said jaw bone when the template has been positioned in said fixed position in the upper or lower jaw.

9. The method according to claim 1, further comprising providing said at least one guide surface with a metal coating extending according to said at least one guide surface.

10. The method according to claim 1, further comprising providing a recess in the template in a position corresponding to said identified at least one bone part, such that the identified at least one bone part extends opposite said recess or through said recess when the template is positioned in the upper or lower jaw, wherein said at least one guide surface extends adjacent to said recess.

11. A method for manufacturing a template, comprising:
generating a digital or physical model of the shape of at least a part of the jaw bone of an upper or lower jaw,
taking into account the data of the model, manufacturing the template such that the template is configured to be placed in a fixed position in the upper or lower jaw,
providing at least one guide surface to guide a milling element,
identifying a desired shape of the jaw bone such that the desired shape is identified such that a prosthetic element fits in the jaw bone, comparing the desired shape to said model,
identifying, based on the comparison, at least one bone part of the jaw bone to be removed from the jaw bone to achieve said desired shape,
providing said at least one guide surface on the template such that, after the template has been positioned in the upper or lower jaw, said at least one guide surface is configured to guide said milling element to remove the identified at least one bone part,
selecting a position and orientation of a bore hole in the jaw bone for placing at least one implant,
defining an opening in said template for guiding a drill to bore said bore hole in the selected position and orientation, wherein a position and orientation for said opening are selected such that, when the template is positioned in the upper or lower jaw in said fixed position, said bore hole is defined by guiding a drill through said opening,
wherein said template is made from at least two parts, wherein a first part forms a basic piece configured to be positioned on said fixed position in the upper or lower jaw when in use and exhibits said at least one guide surface, whereas a second part forms a top piece in which said opening is defined, wherein the method further comprises providing a mounting means configured to mount the top piece in a predetermined position in the basic piece when in use.

12. The method according to claim 11, wherein, the step of generating said digital or physical model comprises fixing reference elements in relation to the bone of the upper or lower jaw, and providing fastening elements on said template configured to detachably attach the template to said reference elements when the template has been positioned in said fixed position in the upper or lower jaw.

13. The method according to claim 11, further comprising determining the position of said identified at least one bone part in relation to said reference elements, wherein the step of providing said at least one guide surface comprises, taking into account said relative position, providing said at least one guide surface on the template in a corresponding relative position in relation to said fastening elements, such that, after the template has been positioned in the upper or lower jaw, said at least one guide surface is in a position to guide said milling element remove the identified at least one bone part.

14. The method according to claim 11, wherein the step of generating said digital or physical model comprises making a three-dimensional image of said upper or lower jaw, and making said template on the basis of said three-dimensional image by applying a rapid-prototyping technique.

15. The method according to claim 11 wherein said at least one guide surface is provided on a surface of a recess on a side of the template which is directed towards said jaw bone when the template is positioned in said fixed position in the upper or lower jaw.

16. The method according to claim 11, further comprising providing said at least one guide surface with a metal coating extending according to said at least one guide surface.

17. The method according to claim 11, further comprising providing a recess in the template in a position corresponding to said identified at least one bone part, such that the identified at least one bone part extends opposite said recess or through said recess when the template is positioned in the upper or lower jaw, wherein said at least one guide surface extends adjacent to said recess.

* * * * *